United States Patent [19]
Frisbie

[11] Patent Number: 5,688,234
[45] Date of Patent: Nov. 18, 1997

US005688234A

[54] APPARATUS AND METHOD FOR THE TREATMENT OF THROMBOTIC OCCLUSIONS IN VESSELS

[75] Inventor: Jeffrey S. Frisbie, San Jose, Calif.

[73] Assignee: Cardiometrics Inc., Mountain View, Calif.

[21] Appl. No.: 592,001

[22] Filed: Jan. 26, 1996

[51] Int. Cl.⁶ .................................................. A61B 17/22
[52] U.S. Cl. .................. 604/22; 604/35; 604/49; 604/96; 606/159
[58] Field of Search ............................. 604/35–36, 41–43, 604/52–53, 96, 105–108, 22, 49; 606/127–28, 194, 159, 180

[56] References Cited

U.S. PATENT DOCUMENTS

| | | | |
|---|---|---|---|
| 4,997,435 | 3/1991 | Demeter | 606/127 |
| 5,030,201 | 7/1991 | Palestrant | 604/22 |
| 5,224,945 | 7/1993 | Pannek, Jr. | 606/180 |
| 5,318,576 | 6/1994 | Plassche, Jr. et al. | 606/159 |
| 5,376,094 | 12/1994 | Kline | 606/127 |
| 5,415,634 | 5/1995 | Glynn et al. | 604/282 |
| 5,419,774 | 5/1995 | Willard et al. | 604/22 |
| 5,462,529 | 10/1995 | Simpson et al. | 604/96 |

Primary Examiner—Mark Bockelman
Assistant Examiner—Ellen S. Tao
Attorney, Agent, or Firm—Flehr Hohbach Test Albritton & Herbert LLP

[57] ABSTRACT

Apparatus for the treatment of a thrombotic occlusion in a vessel of a patient comprising a flexible elongate tubular sheath having proximal and distal extremities. A relatively large lumen defined by a thin flexible wall extends from the proximal extremity to the distal extremity of the tubular sheath so that the distal extremity is open. An occlusion disruption device is slidably and rotatably disposed in the lumen in the tubular sheath and includes a flexible elongate torsionally rigid shaft having a length greater than the length of the tubular sheath and having proximal and distal extremities. The shaft has a guide wire lumen extending from the proximal extremity to the distal extremity. Disruption elements are secured to the distal extremity of the shaft which when rotated disrupt the thrombotic occlusion by causing it to break into pieces. Suction is applied to the lumen in the tubular sheath to aspirate pieces into the large lumen of the tubular sheath to remove them from the vessel of the patient.

10 Claims, 2 Drawing Sheets

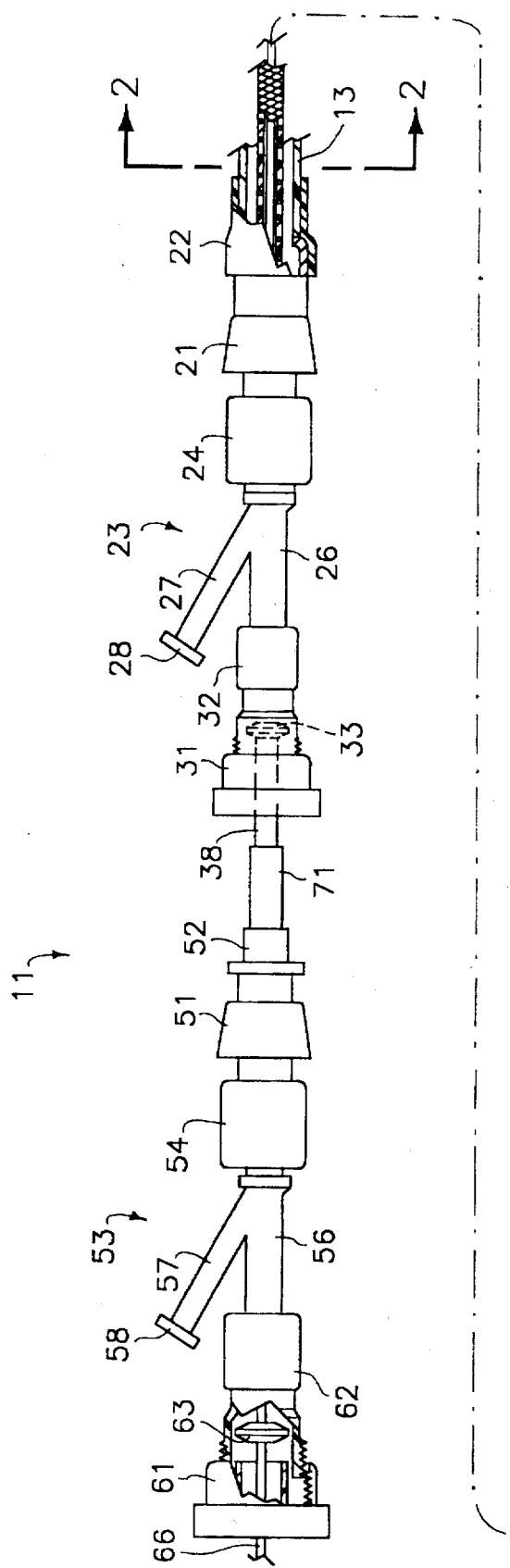
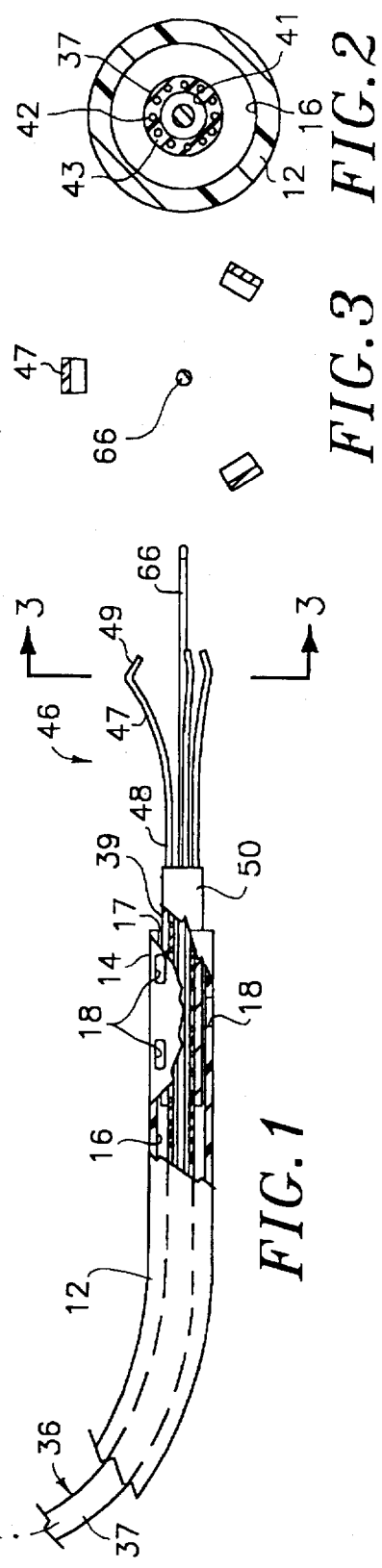

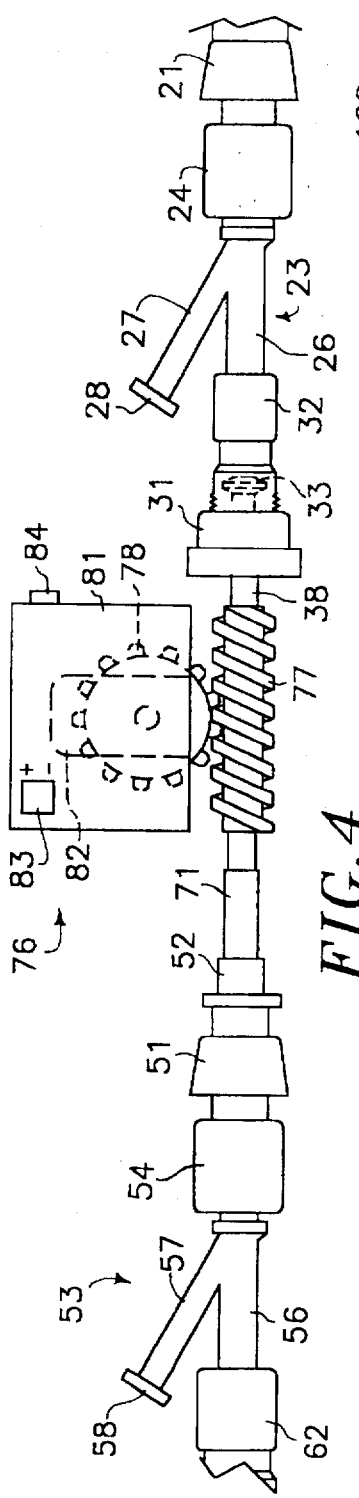
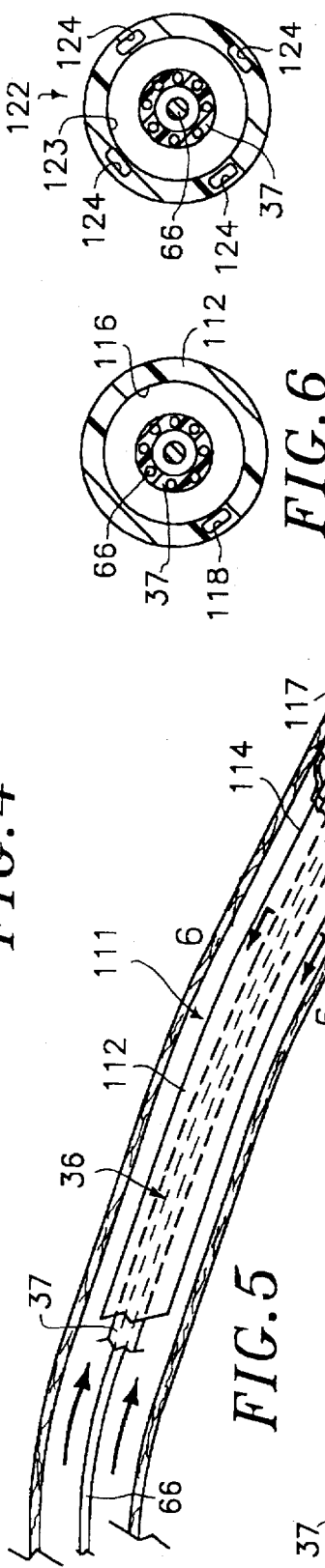
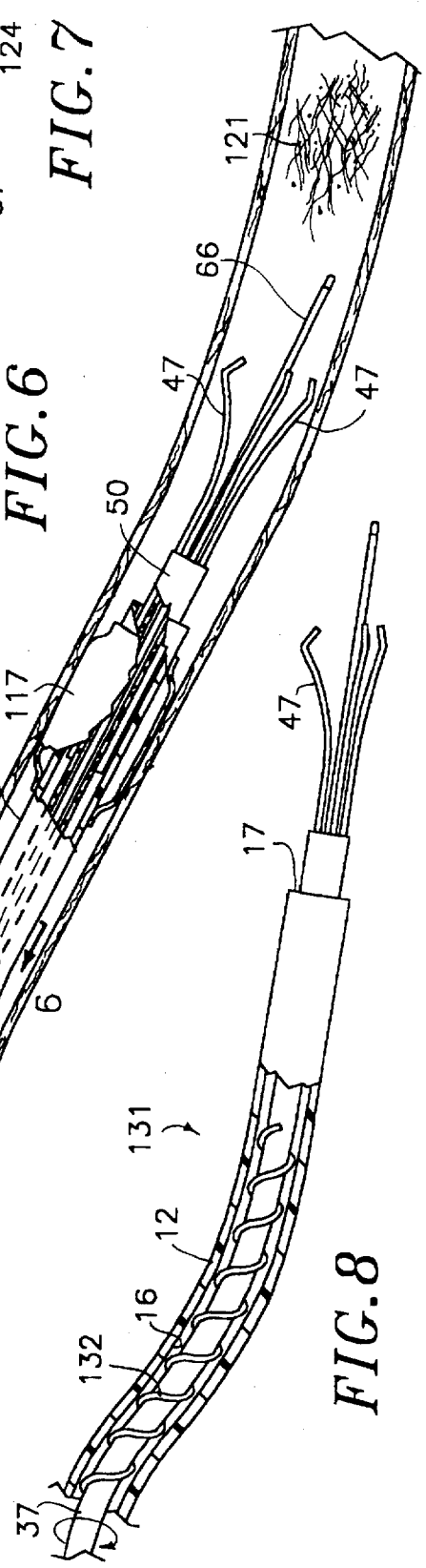

APPARATUS AND METHOD FOR THE TREATMENT OF THROMBOTIC OCCLUSIONS IN VESSELS

This invention relates to an apparatus and method for the treatment of thrombotic occlusions in vessels and particularly to vessels in the heart.

Thrombotic occlusions occur in vessels in the human body and may arise from a number of instigating factors. When a thrombotic occlusion begins to form, blood begins to clot at some particular site in the vessel. Typically, coagulation of blood continues to occur at the site until the vessel in which the clot is being formed is functionally occluded or nearly so. In U.S. Pat. No. 5,419,774 issued on May 30, 1995, there is disclosed a thrombus extraction device in which a negative pressure is created at the distal extremity of the device. A severing mechanism severs the portion of the thrombus which is in a chamber in the device and fluid under pressure is supplied to transport and dilute the blood and thrombus and removing the same from the patient. Attempts have heretofore also been made to remove or decrease the size of thrombus by the use of drugs. There is still a need, however, to remove thrombus more effectively and faster than can be accomplished by the use of drugs. There is also a need for an improved device and method which makes it possible to remove thrombus rapidly and safely in a mechanical manner.

In general it is an object of the present invention to provide an apparatus and method for the treatment of thrombotic occlusions in vessels.

Another object of the invention is to provide an apparatus and method of the above character in which thrombus can be removed quickly and safely.

Another object of the invention is to provide an apparatus and method of the above character in which it is possible to disrupt soft material forming a thrombus but not to disrupt plaque which may be in the vessel in the same vicinity.

Another object of the invention is to provide an apparatus and method of the above character which is atraumatic enough so that plaque in the vessel is not dislodged.

Another object of the invention is to provide an apparatus and method of the above character in which the thrombus is disrupted into particles which can be readily removed by aspiration.

Additional objects and features of the invention will appear from the following description in which the preferred embodiments are set forth in detail in conjunction with the accompanying drawings.

FIG. 1 is a side-elevational view partially in section of an apparatus for the treatment of thrombotic occlusion in vessels incorporating the present invention.

FIG. 2 is a cross-sectional view taken along the line 2—2 of FIG. 1.

FIG. 3 is a cross-sectional view taken along the line 3—3 of FIG. 1.

FIG. 4 is a partial side-elevational view of an embodiment of the proximal portion of the apparatus for the treatment of thrombotic occlusions in vessels incorporating the present invention.

FIG. 5 is a side-elevational view partially in section of another embodiment of an apparatus incorporating the present invention for the treatment of thrombotic occlusions in vessels.

FIG. 6 is a cross-sectional view taken along the line 6—6 of FIG. 5.

FIG. 7 is a cross-sectional view of another embodiment of an apparatus incorporating the present invention for the treatment of thrombotic occlusions in vessels.

FIG. 8 is a side-elevational view partially in section of the distal extremity of another embodiment of an apparatus incorporating the present invention.

In general, the apparatus for treatment of a thrombotic occlusion in a vessel of a patient is comprised of a flexible elongate tubular sheath having proximal and distal extremities and having a relatively large lumen extending from the proximal extremity to the distal extremity with an open distal extremity being defined by a thin flexible wall. An occlusion disruption device is slidably and rotatably disposed in the lumen in the tubular sheath. The occlusion disruption device includes a flexible elongate torsionally rigid shaft having a length greater than the length of the tubular sheath and having proximal and distal extremities. The shaft has a guide wire lumen extending from the proximal extremity to the distal extremity. The occlusion disruption device also includes a plurality of disruption elements secured to the distal extremity of the shaft. Means is coupled to the proximal extremity of the shaft for rotating the shaft and the disruption elements carried thereby for causing disruption of the thrombus in the vessel of the patient to cause it to break into small particles. A flexible guide wire extends through the lumen in the shaft and extends beyond the disruption elements. Means is coupled to the proximal extremity of the tubular sheath for causing a suction to be applied to the lumen in the tubular sheath to aspirate into the lumen in the tubular sheath particles of the thrombus formed by disruption of the thrombus and to remove them from the vessel of the patient.

More in particular, the apparatus 11 for the treatment of thrombotic occlusions consists of a flexible elongate tubular sheath 12 having proximal and distal extremities 13 and 14 and having a relatively large lumen 16 extending from the proximal extremity to the distal extremity and terminating in an open end 17. Additional aspiration holes 18 are provided in the sheath 12 adjacent the open end 17. The sheath 12 should have a length ranging from approximately 90–140 centimeters. In view of the fact that it is desirable to enter vessels having diameters ranging from 2–3 millimeters, the device should have an outside diameter of 2 millimeters and less. Thus, the tubular sheath could have an inside diameter 0.050", a wall thickness of 0.010" and an outside diameter of 0.070". Since it is desirable that the tubular sheath 12 be flexible, the wall thickness could range from 0.008" to 0.015". The tubular sheath 12 should be formed of a suitable flexible material such as plastic. Typically, a plastic having a low coefficient of friction as for example TEFLON should be utilized. Also, it should be appreciated that if desired a layered sheath construction can be used with outer and inner layers of different materials.

A Luer-type fitting 21 is mounted on the proximal extremity 13 of the tubular sheath 12 and is provided with a strain relief fitting 22. A wye 23 of a conventional type is secured to the Luer fitting 21 and is provided with a male Luer fitting 24 removably secured to the female Luer fitting 21. The wye 23 is provided with a central arm 26 and a side arm 27. Both the central arm 26 and side arm 27 are provided with female Luer fittings 28. A Tuohy-Borst adapter 31 provided with a male Luer fitting 32 is removably secured to the female Luer fitting 28 provided on the central arm. 26. The Tuohy-Borst adapter 31 is provided with a conventional o-ring seal 33 which is adapted to form a fluid-tight seal with respect to an occlusion disruption device 36 that is slidably and rotatably mounted in the tubular sheath 12.

It should be appreciated that if desired, the fitting 21, the strain relief 22, the wye 23 and the adapter 31 can be fabricated as a single unit incorporating the side arm 27 and the seal 33. Alternatively, only the wye 23 and the adapter 31 can be combined into a single unit. Also, if desired, a rotatable joint (not shown) can be provided between parts to permit rotation of one part with respect to another part.

The occlusion disruption device 36 consists of a flexible elongate torsionally rigid shaft 37 having proximal and distal extremities 38 and 39 and is provided with a guide wire lumen 41 extending from the proximal extremity to the distal extremity. The shaft 37 has a length which is substantially greater than the length of the tubular sheath 12, as for example from 10–25 centimeters. It is preferably of a small diameter so as to maintain a low profile while still being torsionally rigid so that it can be rotated from the proximal end and still obtain good control of the rotation at the distal extremity 39. The guide wire lumen 41 is sized so that it can receive conventional guide wires as for example 0.014" to 0.018" guide wires. Thus to accommodate a 0.014" guide wire, the lumen 41 should have an inside diameter of 0.016" to 0.017" and if it is desired to accommodate a 0.018" guide wire, it should have an inside diameter ranging from 0.020" to 0.021".

The shaft 37 consists of a multi-strand cross-wound braid of a suitable material such as stainless steel or NYLON extending the length of the shaft 37 which is overlaid and embedded with a polyimide plastic. The braid 42 can be formed of a wire of a suitable diameter, as for example 0.002" through which the polyimide 43 has been overlaid and embedded therein so as to provide a thin-walled flexible yet torsionally rigid shaft 37. Typically the shaft 37 has a wall thickness of 0.004" to 0.008" to provide an outside diameter for the shaft 37 which can range from 0.024" to 0.037".

A disruption assembly 46 is secured to the distal extremity 39 of the shaft 37 and consists of at least three circumferentially spaced-apart prongs 47 which have proximal extremities 48 that are secured to the distal extremity of the shaft 37 by shrink tube 50 or other suitable means and distal extremities 49 which are curved as shown in FIG. 1 in such a manner so that they are bowed outwardly and then are inclined inwardly as shown in FIG. 1. The prongs 47 are formed of a suitable material such as a stainless steel or platinum alloy and can have a suitable length, as for example 2 centimeters and a suitable cross-sectional area such as 0.008" in width and 0.004" in thickness. Alternatively, they can have a circular or ovate cross-sectional area.

The prongs 47 are provided with a spring-like characteristic to provide the shape which is shown in FIG. 1. They are sufficiently flexible so that they can be retracted into the sheath lumen 16 during the time that the occlusion disruption device 36 is being inserted into the vessel of the patient as hereinafter described. By controlling the amount of the advancement of the prongs 47 from the distal extremity of the tubular sheath 12, it is possible to control the expansion diameter so that they are of an appropriate size for the vessel of interest in which the device is to be used. Typically, the diameter of the disruption assembly 46 should be such so that it is not in an overexpanded position which is greater than the vessel being treated. Thus, the diameter of the disruption assembly 46 should correspond to the interior diameter of the vessel being treated. In this way, the disruption assembly 46 will not cause undue trauma to the vessel when the disruption assembly 46 is rotated. In addition, since the distal extremities of the prongs 47 are curved inwardly as shown, they will not cause trauma to the vessel of the patient. In this way, the disruption assembly 46 can be placed in a safe condition for disruption of a thrombus in a vessel as hereinafter described.

It has been found that in order to provide maximum disruptive trajectories for the prongs of the disruption assembly 46, it is desirable that the prongs 47 have slightly different lengths. For example, two of the prongs 47 can have approximately the same length whereas the third prong can be several millimeters shorter than the other prongs so that when the prongs are rotated, they will rotate through slightly different arcs and thereby encounter different parts of the thrombus in the vessel to thereby maximize the disruption of the thrombus. As the prongs 47 are advanced into the vessel during disruption of a thrombus, the amount of disruption and speed of disruption can be ascertained by placing calibration marks (not shown) on the proximal extremity of the shaft 37 so that the amount of advancement and retraction of the device relative to the tubular sheath 12 can be ascertained during operation of the disruption assembly 46. Also, at any given position of advancement of the disruption assembly 46 relative to the sheath 12, it may be desirable to advance or retract the disruption device 36 and the sheath 12 as a unit. At these times, the amount of advancement or retraction can be ascertained by placing calibration marks [not shown] on the proximal extremity 13 of the sheath 12.

A female Luer fitting 51 is mounted on the proximal extremity 38 of the shaft 37 and is provided with a strain relief fitting 52. A wye adapter 53 is provided with a male Luer fitting 54 that is removably secured to the female Luer fitting 51. The wye adapter 53 is provided with a central arm 56 and a side arm 57 which are provided with female Luer fittings 58. A Tuohy-Borst adapter 61 of the type hereinbefore described is provided and has a male Luer fitting 62 removably secured to the female fitting 58 on the central arm 56 and is provided with an O-ring 63 which is adapted to form a fluid-tight seal with respect to a conventional guide wire 66 slidably mounted therein. The guide wire 66 as hereinbefore described can be of a suitable size, as for example 0.014" or 0.018" and have a length which is substantially greater than the length of the occlusion disruption device 36.

Means is provided for causing rotation of the occlusion disruption device 36 and can be in the form of a cylindrical member 71 secured to the proximal extremity 38 of the shaft 37. Suitable means such as a shrink fit or an adhesive (not shown) can be used for securing the member 71 to the shaft 37. The member 71 is adapted to be engaged by two fingers of the hand so that it can be manually rotated by the user of the device at a suitable speed, as for example 10 revolutions per minute or greater. Alternatively as shown in FIG. 4, a motor-driven mechanism 76 can be provided for rotating the shaft 37 with more control and at greater speeds, as for example speeds ranging from 300–500 rpm. As shown, such a mechanism 76 can consist of a worm 77 secured to the proximal extremity 38 of the shaft 37 that engages a worm gear 78. The worm gear 78 is rotatably mounted in a housing 81 and can be coupled to the shaft 37. The worm gear 78 is driven by a small electric motor 82 mounted the housing and supplied with power from a battery 83 under the control of an on/off switch 84. If desired, variable speed control and display features can be incorporated.

Operation and use of the apparatus 11 may now be briefly described as follows. Let it be assumed that a person is having or has had a heart attack or is experiencing heart attack symptoms such as chest pain. Also let it be assumed that the patient has been subjected to an angiographic analysis during which time it is found that there is a thrombotic occlusion in a vessel, as for example in one of the coronary arteries and that it is causing the chest pain. Let it also be assumed that it is desired to conduct a procedure of the type described in the present invention to remove the thrombus from the vessel of the patient. This is accomplished by advancing a standard guiding catheter into the femoral artery to the ostium of the artery of interest. A guide wire 66 of the type hereinbefore described is then advanced into the guiding catheter up to the thrombus or clot in the vessel. If the thrombus or clot completely occludes the vessel, it may not be possible to pass the guide wire through the clot. Even if it does not completely occlude the vessel, it may not be desirable to pass the guide wire through the clot because of the danger of dislodging a piece of the thrombus.

Prior to or immediately after insertion of the guide wire 66 into the desired location, the occlusion disruption device 36 is inserted into the lumen 16 of the tubular sheath 12 so that the prongs 47 are retracted within the distal extremity of the sheath. The occlusion disruption device 36 and the tubular sheath 12 can then be advanced as a unit over the guide wire which is inserted through the guide wire lumen 41 in the shaft 37. The unit consisting of the occlusion disruption device 36 and the tubular sheath 12 is advanced until the distal extremity 14 of the sheath is in the region of interest in close proximity to the thrombus in the vessel. As soon as this has been accomplished, the proximal extremity of the shaft 37 of the occlusion disruption device 36 is grasped by the hand while holding the tubular sheath 12 in the other hand and progressively advancing the shaft 37 so that its distal extremity 39 extends beyond the distal extremity 14 of the tubular sheath 12. The Tuohy-Borst adapter 31 is then tightened if necessary to form a nearly fluid-tight seal with the o-ring 33 disposed about the shaft 37 of the occlusion disruption device 36.

As the shaft 37 is advanced, the prongs 47 as soon as they clear the tubular sheath begin to spring yieldably outwardly toward engagement with the side wall of the vessel. The positions of the prongs 47 can be viewed fluoroscopically. As hereinbefore described, the amount of advancement of shaft 37 relative to the sheath 12 can be ascertained by the use of calibration marks on the proximal extremity of shaft 37.

As soon as the prongs 47 have cleared the tubular sheath 12, the shaft 37 can be rotated by grasping the cylindrical member 71 between two fingers of the hand and rotating the same in either a clockwise or counter-clockwise direction to commence disruption of the thrombus while not disrupting or dislodging plaque which may be in the vessel. Prior thereto, or at least during soft material of the time that the prongs 47 are being rotated, a suction is applied to the aspiration side arm 27 of the wye fitting 23 so that as particles are dislodged from the thrombus by the rotating prongs 47, the pieces of debris which are dislodged are immediately aspirated through the opening 17 in the distal extremity 14 of the tubular sheath 12 as well as through the aspiration holes 18 in the side wall of the tubular sheath 12 immediately adjacent the distal extremity as shown in FIG. 1. During this time, the prongs 47 rotate about the guide wire 66 with the distal extremity of the guide wire 66 being retracted inside the distal extremity of shaft 37 or just distal of the distal extremities 49 of the prongs 47. The guide wire 66 can be advanced through the thrombus or clot as suction is being applied to the region just distal of the tubular sheath 12. As pointed out previously, care must be taken not to cause inadvertent destruction of the clot unless it is clear that suction is present to remove from the vessel any portions of the clot or thrombus which may be dislodged by movement of the guide wire 66. Care also should be taken not to place an excessive vacuum in the vessel which can possibly cause collapse of the blood vessel. In order to inhibit or prevent any particles of the thrombus or clot from washing downstream, it may be desirable to occlude the vessel in which the procedure is taking place just proximal of the clot or thrombus as hereinafter described.

The prongs 47 are continued to be rotated and advanced simultaneously until the distal extremities 49 have passed beyond the clot or thrombus, thereby ensuring that the clot or thrombus has been completely disrupted and aspirated from the vessel.

As soon as thrombus removal has been accomplished, the occlusion disruption device 36 can be retracted so that the prongs 47 are compressed and brought within the distal extremity of the tubular sheath 12. As soon as this has been accomplished, the tubular sheath 12 with the occlusion disruption device 36 therein can be removed from the vessel over the guide wire 66. Alternatively, the guide wire 66 can also be removed at the same time assuming that the desired procedure has been accomplished. The entrance to the femoral artery can then be sutured in a conventional manner.

As explained previously, rather than manually rotating the shaft 37 to cause disruption of the thrombus or clot, this can be accomplished by the motor-driven mechanism 76 hereinbefore described as soon as the prongs 47 have been displaced from the distal extremity of the sheath 12. The remainder of the procedure is very similar to that hereinbefore described in connection with the manually rotated shaft 37.

In FIGS. 5–6, there is disclosed another embodiment of an apparatus 111 which includes a tubular sheath 112 that is very similar to the tubular sheath 12. It is provided with a lumen 116 extending from the proximal extremity to the distal extremity. An inflatable balloon 117 is provided on the distal extremity 114 and is formed of a suitable elastomeric or non-elastomeric material depending upon the characteristics desired. The tubular sheath 112 is provided with a balloon inflation lumen 118 which opens into the interior of the balloon 117 through a balloon inflation port (not shown) to permit inflation of the balloon when the distal extremity 114 is disposed in the appropriate location near a thrombus 121 as shown in FIG. 5. Inflation of the balloon 117 prevents particles dislodged from the thrombus 121 by the prongs 47 from flowing downstream. Since the thrombus is already causing ischemia to the patient, the inflation of the balloon 117 should not greatly increase the ischemia. The prongs 47 of the occlusion disruption device 36 are rotated in the manner hereinbefore described. If the flow of blood is as depicted in FIG. 5 from left to right, the timing of suction may be adjusted to coincide with deflation of the balloon. Once the thrombus has been disrupted and removed and the balloon 117 deflated, the tubular sheath 112 along with the occlusion disruption device 36 can be removed from the vessel of the patient. In such a procedure, the balloon can remain inflated for 20–30 seconds and possibly as long as several minutes without compromising the patient.

In FIG. 7 there is shown another embodiment of the invention in which a tubular sheath 122 is provided having a centrally disposed lumen 123 extending therethrough. In addition, there are provided lumens 124 which are disposed in the side wall forming the sheath 122. As shown, four of such lumens 124 have been provided so that additional lumens are available for delivering liquids, drugs and the like. For example, in addition to or instead of a balloon inflation lumen the other lumens can be used as drug delivery lumens or liquid delivery lumens which can carry drugs or liquids during the time that the procedure of the present invention is being undertaken.

It should be appreciated that measurement of pressure of the blood in the vessel can be made by conventional means through one of the lumens 124. Alternately a conventional pressure sensing guide wire can be utilized in place of the guide wire 66.

It should also be appreciated that although the prongs 47 have distal extremities which are free that if desired, the distal extremities can be interconnected to provide an egg beater-like configuration. With such a construction, the thrombus or clot will be disrupted from the center outwardly with the disrupted particles being sucked out of the vessel in a manner hereinbefore described.

In the present invention, when the assembly 46 is extended outward through opening 17 of the distal extremity 14 of sheath 12, the prongs 47 typically expand to a diameter that is predetermined and fixed. Therefore, a user of the apparatus of the present invention would select a certain model of different size models of the apparatus depending on the estimated diameter of the vessel to be treated.

An alternative is to control the amount of radial expansion of the prongs by limiting the amount to which the prongs 47 extend out of or are partially deployed from the opening 17.

Still another embodiment of the present invention is shown in FIG. 8 in which the distal extremity of an apparatus 131 is shown. It is very similar to the embodiment shown in FIG. 1 and includes the flexible sheath 12. The occlusion disruption device 36 has been modified to include a helix 132 formed on the outer surface of the shaft 37 and extending the length thereof. The helix 132 can be formed integral with the outer surface or can be formed separately and adhered to the outer surface of shaft 37 by suitable means, such as an adhesive. The helix 132 serves as a worm to cause particulate dislodged by the prongs 47 of the disruption assembly 46 to be moved from the distal extremity to the proximal extremity of the shaft 37 as the shaft 37 is rotated in the appropriate direction thereby carrying the pieces of the disrupted thrombus from the distal extremity to the proximal extremity of the shaft.

It is apparent from the foregoing that there has been provided an apparatus for the treatment of thrombolytic occlusions in the vessels of a patient which makes it possible to disrupt the thrombus or clot with great rapidity to interrupt a heart attack which may be occurring. The apparatus is of a relatively simple construction and is relatively simple to operate.

What is claimed:

1. Apparatus for use with a guide wire for the treatment of a thrombotic occlusion in a patient having a vessel with thrombus and plaque therein and capable of being advanced to said thrombotic occlusion comprising a flexible elongate tubular sheath having proximal and distal extremities and having a relatively large lumen extending from the proximal extremity to the distal extremity so that the distal extremity is open and the lumen is defined by a thin flexible wall, a thrombotic occlusion disruption device slidably and rotatably disposed in the lumen in the tubular sheath, said thrombotic occlusion disruption device including a flexible elongate torsionally rigid shaft having a length greater than the length of the tubular sheath and having proximal and distal extremities, the shaft having a guide wire lumen extending from the proximal extremity to the distal extremity of the shaft and sized to receive the guide wire, said shaft being sufficiently flexible so that it can be advanced over and follow said guide wire to the thrombotic occlusion in a vessel, a plurality of distally extending prong shaped disruption elements having proximal and distal extremities means securing the proximal extremities of the disruption elements to the distal extremity of the shaft, the distal extremities of the disruption elements being movable between retracted positions when disclosed in the lumen of the tubular sheath and expanded positions when disposed outside the lumen of the tubular sheath, means coupled to the proximal extremity of the shaft for rotating the shaft and the disruption elements carried thereby, said disruption elements being rigid enough so that during rotation the thrombotic occlusion in the vessel of the patient is disrupted by causing it to break into smaller pieces, said disruption elements also being flexible enough so that during rotation the plaque in the vessel is left intact and means coupled to the proximal extremity of the tubular sheath for aspirating into the large lumen of the tubular sheath pieces of the thrombotic occlusion and removing them from the vessel of the patient.

2. Apparatus as in claim 1 further comprising a balloon mounted on the distal extremity of the tubular sheath, said balloon being proximal of the plurality of when the plurality of are in the expanded position and means carried by the tubular sheath for inflating and deflating the balloon.

3. Apparatus for use with a guide wire for the treatment of a thrombotic occlusion in a patient having a vessel with thrombus and plaque therein and capable of being advanced to said thrombotic occlusion comprising a flexible elongate tubular sheath having proximal and distal extremities and having a relatively large lumen extending from the proximal extremity to the distal extremity so that the distal extremity is open and the lumen is defined by a thin flexible wall, a thrombotic occlusion disruption device slidably and rotatably disposed in the lumen in the tubular sheath, said thrombotic occlusion disruption device including a flexible elongate torsionally rigid shaft having a length greater than the length of the tubular sheath and having proximal and distal extremities. the shaft having a guide wire lumen extending from the proximal extremity to the distal extremity of the shaft and sized to receive the guide wire, said shaft being sufficiently flexible so that it can be advanced over and follow said guide wire to the thrombotic occlusion in a vessel, a plurality of disruption elements having proximal and distal extremities, means securing the proximal extremities of the disruption elements to the distal extremity of the shaft, the distal extremities of the disruption elements being movable between retracted positions when disposed in the lumen of the tubular. sheath and expanded positions when disposed outside the lumen of the tubular sheath, means coupled to the proximal extremity of the shaft for rotating the shaft and the disruption elements carried thereby, said disruption elements being rigid enough so that during rotation the thrombotic occlusion in the vessel of the patient is disrupted by causing it to break into smaller pieces, said disruption elements also being flexible enough so during rotation the plaque in the vessel is left intact, said shaft also having an outer surface, said outer surface being provided with a helix for carrying the smaller pieces of the thrombotic occlusion from the distal extremity to the proximal extremity of the shaft and means coupled to the proximal extremity of the tubular sheath for aspirating into the large lumen of the tubular sheath pieces of the thrombotic occlusion and removing them from the vessel of the patient.

4. Apparatus as in claim 1 wherein said disruption elements are formed of a radiopaque material.

5. Apparatus as in claim 1 wherein said disruption elements have inwardly turned distal extremities.

6. Apparatus as in claim 1 wherein said disruption elements are spaced apart circumferentially.

7. Apparatus as in claim 1 together with additional lumens formed in the tubular sheath.

8. A method for treatment of thrombotic occlusions in a patient having a vessel with thrombus and plaque therein by the use of a flexible tubular sheath having proximal and distal extremities with a lumen extending from the proximal extremity to the distal extremity, a thrombotic occlusion disruption device slidably and rotatably disposed within the lumen of the sheath, said disruption device having a shaft with proximal and distal extremities and a guide wire lumen extending from the proximal extremity to the distal extremity of the shaft, distally extending prong shaped disruption elements having poroximal and distal extremities, means securing the proximal extremities of the disruption elements to the distal extremity of the shaft, the distal extremities of the disruption elements being movable between retracted positions when disposed in the lumen of the tubular sheath and expanded positions when disposed outside the lumen of the tubular sheath, the method comprising providing a guide wire having a distal extremity, the method comprising inserting the guide wire into the vessel of a patient through said shaft until the distal extremity of the guide wire is in the proximity of the thrombotic occlusion in the vessel of the patient, advancing the occlusion disruption device out of the tubular sheath so that the disruption elements are exposed, causing rotation of the disruption elements while advancing the same through the thrombotic occlusion to cause disruption of the thrombotic occlusion into pieces, applying suction from the tubular sheath to aspirate the pieces dislodged from the thrombotic occlusion and withdrawing the occlusion disruption device from the vessel while leaving the plaque intact inside the vessel.

9. A method as in claim 8 wherein said shaft is rotated at a speed from 10 rpm to 500 rpm.

10. Apparatus for use with a guide wire for the treatment of a thrombotic occlusion in a patient having a vessel with thrombus and plaque therein and capable of being advanced to said thrombotic occlusion comprising a flexible elongate tubular sheath having proximal and distal extremities and having a relatively large lumen extending from the proximal extremity to the distal extremity so that the distal extremity is open and the lumen is defined by a thin flexible wall, a thrombotic occlusion disruption device slidably and rotatably disposed in the lumen in the tubular sheath, said thrombotic occlusion disruption device including a flexible elongate torsionally rigid shaft having a length greater than the length of the tubular sheath and having proximal and distal extremities, the shaft having a guide wire lumen extending from the proximal extremity to the distal extremity of the shaft and sized to receive the guide wire, said shaft being sufficiently flexible so that it can be advanced over and follow said guide wire to the thrombotic occlusion in a vessel, a plurality of distally extending prong shaped disruption elements secured to the distal extremity of the shaft, means coupled to the proximal extremity of the shaft for rotating the shaft and the disruption elements carried thereby, said disruption elements being rigid enough so that during rotation the thrombotic occlusion in the vessel is disrupted by causing it to break into smaller pieces, said disruption elements also being flexible enough so that during rotation the plaque in the vessel is left intact and means coupled to the proximal extremity of the tubular sheath for aspirating into the large lumen of the tubular sheath pieces of the thrombotic occlusion and removing them from the vessel of the patient.

\* \* \* \* \*